United States Patent [19]

Kitaoka et al.

[11] 4,056,631

[45] Nov. 1, 1977

[54] METHOD OF COMBATTING TICKS

[75] Inventors: Shigeo Kitaoka, Musashino; Katsuhiro Johkoh, Yokohama; Hisashi Ebisawa; Tadashi Sato, both of Tokyo; Hiroshi Kubo; Sosuke Takahashi, both of Yokohama; Yoshinobu Kawase, Tokyo, all of Japan

[73] Assignee: Showa Denko K.K., Tokyo, Japan

[21] Appl. No.: 693,833

[22] Filed: June 8, 1976

Related U.S. Application Data

[63] Continuation-in-part of Ser. No. 515,929, Oct. 18, 1974, Pat. No. 3,995,053.

[30] Foreign Application Priority Data

Oct. 23, 1973 Japan ............................ 48-118458

[51] Int. Cl.$^2$ ........................ A01N 9/06; A01N 9/20; A01N 9/24

[52] U.S. Cl. .................................... 424/330; 424/304

[58] Field of Search ............................... 424/304, 330

[56] References Cited

U.S. PATENT DOCUMENTS

| | | | |
|---|---|---|---|
| 3,175,896 | 3/1965 | Arndt et al. | 424/330 |
| 3,852,437 | 12/1974 | Helfenberger | 424/304 |
| 3,855,292 | 12/1974 | Wollweber et al. | 424/304 |

*Primary Examiner*—Albert T. Meyers

*Assistant Examiner*—D. W. Robinson

*Attorney, Agent, or Firm*—Sherman & Shalloway

[57] ABSTRACT

Method of combatting ticks which comprises applying to the surface of the body of domestic animals an effective amount of a carbodiimide of the formula $$C_6H_5-C(CH_3)_2-N{=}C{=}N-R$$

wherein R represents the specified groups.

17 Claims, No Drawings

METHOD OF COMBATTING TICKS

This is a continuation-in-part application of Ser. No. 515,929 filed on Oct. 18, 1974, now U.S. Pat. No. 3,995,053.

This invention relates to a method of combatting ticks which comprises applying to the surface of the body of domestic animals infested with ticks an effective amount of a carbodiimide of the formula

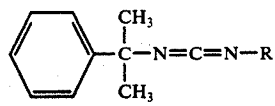

I wherein R is a member selected from the class consisting of: (1) acyclic alkyl groups containing 2–18 carbon atoms; (2) a cyclohexyl group and a cyclohexyl group substituted by 1-3 methyl groups; (3) a phenyl group and a phenyl group substituted by at least one substituent of the group consisting of alkyl groups of 1-4 carbon atoms, alkoxy groups of 1-4 carbon atoms and chlorine atom; (4) a benzyl, a p-chlorobenzyl and a phenylethyl group; and (5) a furfuryl group.

The carbodiimides of the formula I defined above are referred to herein as the compounds of the invention.

It has now been found that the compounds of the invention have superior pesticidal power against a wide variety of hygienic and agricultural pests and especially that their exterminatory action against acarri and harmful insects, and particularly against ticks is outstanding. Acarri which infest on domestic animals are called as ticks.

Typical acarri that live on livestocks, are such ticks as *Boophilus spp.* and *Haemaphysalis spp.* Since these ticks cause exceedingly great damages, there has been strong demand for a long time for a powerful chemical that can exterminate these ticks or prevent their development.

The object of the present invention is to provide a method of combatting ticks effectively.

The compounds of the invention have an effective action against all stages of development, i.e., the egg, larval and adult stages, of ticks. And a surprising fact is that the compounds of the invention have even the action or destroying the ovipositing ability of ticks. The *Boophilus spp.*, which lives on livestock and also serves as a vector of pathogenic piroplasma, lays its eggs in pastures where the eggs hatch into larvae and then infest, say, cattle. The larvae develop into adults on the body of cattle. The tick has a considerably large body. The female has a body length of about 8 millimeters, while the male is about 3 millimeters long. The ability of this tick to survive is great. Various compounds have so far been employed for combatting ticks. Generally, these compounds are applied in a concentration of 0.025–1%. On the contrary the compounds of the invention can usually destroy the eggs of ticks with a given concentration, say, a concentration of about 15 ppm, and the oviposition itself can be inhibited by the application of the compounds of the invention to the surface of the body of animals infested with ticks or to pastures at such a low concentration that does not destroy the eggs. Hence, it is possible to prevent development of ticks from the very beginning and exterminate them without allowing their growth to adult. This is one of the great features of the compounds of the invention.

The toxicity of the compounds of the invention to mammals is extremely low, and again it causes practically no harm to plants. In a test conducted by oral administration of the compounds of the invention to mice, the $LD_{50}$ was in almost of all instances more than 4000 mg/Kg, some compounds exhibiting even as high as about 15,000 mg/Kg.

Toxicity to mammals of Chlorpyrifos as a typical of heretofore known effective tickicides is considerably high, e.g., 70 mg/Kg at $LD_{50}$ for mice.

The compounds of the invention, which are usually nonvolatile liquids, can be applied as such, or after dilution with diluents or fillers, to the place of origin of the ticks or the place of their infestation. In using the compounds of the invention in a diluted state, they can be used in the following manner. For instance, they can be used as a wettable powder by mixing and comminuting them along with an emulsifier and a solid filler, following which the so obtained powder is suspended in water at the time of their use. They can be used as an emulsion by dissolving them in an organic solvent along with an emulsifier followed by dilution with water at the time of their use. Further, they can be used in the forms of an oil preparation by merely dissolving them in an organic solvent. Again, they can be impregnated in solid fillers and used as dusting powders, granules, and tablets. As examples of the usable carrier materials, fillers and organic solvents, included are such materials as clay, talc, bentonite, diatomaceous earth, starch, kaolin, benzene, xylene, kerosene, ketones, dimethylformamide, Freon, etc. In the case of the wettable powder and emulsion, the compounds of the invention are applied diluted to usually about 1/100 to about 1/3000 of their original strength. On the other hand, in the case of the dusting powders, granules and tablets, these are applied in a state wherein the compounds of the invention are contained therein in a concentration of about 0.5 to about 10%. The application can be made by such procedures as dipping, spraying, dusting, scattering and the like. While some of the compounds of the invention are new, they can all be prepared in a simple manner by conventional processes. For example, these compounds can be obtained by dehydrosulfurizing the thiourea derivative of the formula

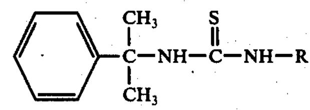

with either NaOCl, HgO, PbO or $PbCO_3$, or by submitting the urea derivative of the formula

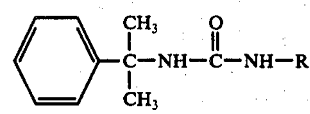

to a dehydration reaction using p-toluene sulphonyl chloride in pyridine or by using $P_2O_5$.

Two specific examples illustrating the suynthesis of the present invention will be given below.

Synthesis of N-n-octyl-N'-(2-phenyl-2-propyl)carbodiimide

A mixture of 14.2 grams of N-n-octyl-N'-(2-phenyl-2-propyl)-thiourea, 20 grams of basic lead carbonate and 100 ml of dry xylene was heated under reflux for 3 hours. The reaction liquid was then separated by filtration followed by concentration of the mother liquor, whereupon N-n-octyl-N'-(2-phenyl-2-propyl)carbodiimide of high purity was obtained. When this was distilled further, 10.1 grams of the intended product of b.p. 121°-3° C./0.15 mmHg was obtained as a pure product.

Synthesis of N-p-methoxy-o-tolyl-N'-(2-phenyl-2-propyl)carbodiimide

A mixture of 6.0 grams of N-(p-methoxy-o-tolyl)-N'-(2-phenyl-2-propyl)-urea, 5.7 grams of p-toluene sulfonyl chloride and 30 ml of pyridine was reacted for 2 hours at 60° C. The reaction mixture was then cooled with ice to separate out the pyridine salt, after which the precipitated salt was filtered off, and the mother liquor was concentrated. Xylene was added, and the residual salt was filtered off. When the mother liquor was then concentrated, the intended product was obtained in high purity. The yield was 4.1 grams.

Specific examples of desirable compounds of the invention include the following compounds. For convenience of reference, the compounds have been numbered.

Compound No.

1. N-ethyl-N'-(2-phenyl-2-propyl)carbodiimide
2. N-n-propyl-N'-(2-phenyl-2-propyl)carbodiimide
3. N-iso-propyl-N'-(2-phenyl-2-propyl) carbodiimide
4. N-tert-butyl-N'-(2-phenyl-2-propyl)carbodiimide
5. N-n-pentyl-N'-(2-phenyl-2-propyl)carbodiimide
6. N-n-hexyl-N'-(2-phenyl-2-propyl)carbodiimide
7. N-n-heptyl-N'-(2-phenyl-2-propyl)carbodiimide
8. N-n-octyl-N'-(2-phenyl-2-propyl)carbodiimide
9. N-(2-ethyl-n-hexyl)-N'-(2-phenyl-2-propyl)carbodiimide
10. N-n-nonyl-N'-(2-phenyl-2-propyl)carbodiimide
11. N-n-decyl-N'-(2-phenyl-2-propyl)carbodiimide
12. N-n-dodecyl-N'-(2-phenyl-2-propyl)carbodiimide
13. N-n-myristyl-N'-(2-phenyl-2-propyl)carbodiimide
14. N-n-cetyl-N'-(2-phenyl-2-propyl)carbodiimide
15. N-n-stearyl-N'-(2-phenyl-2-propyl)carbodiimide
16. N-cyclohexyl-N'-(2-phenyl-2-propyl)carbodiimide
17. N-(3,3,5-trimethylcyclohexyl)-N'-(2-phenyl-2-propyl)carbodiimide
18. N-phenyl-N'-(2-phenyl-2-propyl)carbodiimide
19. N-p-tolyl-N'-(2-phenyl-2-propyl)carbodiimide
20. N-p-methoxyphenyl-N-'-(2-phenyl-2-propyl)carbodiimide
21. N-p-methoxy-o-tolyl-N'-(2-phenyl-2-propyl)carbodiimide
22. N-3,4-dichlorophenyl-N'-(2-phenyl-2-propyl)carbodiimide
23. N-benzyl-N'-(2-phenyl-2-propyl)carbodiimide
24. N-α-phenylethyl-N'-(2-phenyl-2-propyl)carbodiimide
25. N-β-phenylethyl-N'-(2-phenyl-2-propyl)carbodiimide
26. N-p-chlorobenzyl-N'-(2-phenyl-2-propyl)carbodiimide
27. N-furfuryl-N'-(2-phenyl-2-propyl)carbodiimide Among the above-mentioned compounds, those compounds of the formula I wherein R is a member of the following group have the most strong activity;

R: an acrylic alkyl group of $C_6$–$C_{12}$: a cyclohexyl or a cyclohexyl group substituted by 1–3 methyl groups; a benzyl group; and a phenethyl group;

Of these, most preferred are Compounds Nos. 6–12; Nos. 16–18; and Nos. 23–26.

Recipes of the tickicidal compositions of the invention are shown below. In the recipes the parts are on a weight basis.

| Recipe 1 (emulsion) | Parts |
|---|---|
| Compound No. 10 | 50 |
| Xylene | 15 |
| Nonionic emulsifier (SORPOL, a product of Toho Chemical Co., Japan) | 35 |

The foregoing ingredients are mixed and rendered into an emulsion. In using this emulsion, it is diluted with water and applied.

| Recipe 2 (wettable powder) | Parts |
|---|---|
| Compound No. 6 | 20 |
| Diatomaceous earth-clay mixture | 75 |
| Polyoxyethylenealkylphenol ether type emulsifier | 5 |

The foregoing ingredients ae rendered into a wettable powder by mixing and comminuting the ingredients. In using this wettable powder, it is suspended in water and applied.

| Recipe 3 (dusting powder) | Parts |
|---|---|
| Compound No. 7 | 2 |
| Talc-clay mixture | 98 |

The foregoing ingredients are rendered into a dusting powder by mixing and comminuting the ingredients. This is directly applied.

Next, there will be shown the tests that were conducted to determine the effectivenss of the tickicidal compositions of the invention.

TEST 1

Test of the effectiveness in inhibiting the oviposition by *Boophilus microplus and Haemaphysalis longicornis*

One each of the adults of female *Boophilus microplus* or *Haemaphysalis longicornis* which had been allowed to suck blood fully was placed in a flat bottom test tube having a diameter of 10 millimeters and a depth of 35 millimeters. After rendering the chemicals to be tested into acetone solutions, the solutions were dropped to the back of the ticks in an amount corresponding to 110 gamma per one gram of body weight, using a micro syringe after which the acetone was evaporated. The test tube was then transferred to a desiccator containing a small portion of water where it was left standing at a constant temperature of 30° C., and the ticks were allowed to oviposit. Two weeks later, the amount of eggs laid per 1 gram of body weight was counted. Using this value and the amount of eggs laid in the case of the control group not treated with the chemicals, the rate of inhibition of oviposition was obtained as follows:

$$\text{Inhibition ratio of oviposition} = \frac{A - B}{A} \times 100$$

where

*A* is the number of eggs laid per gram of body weight of ticks of the group not treated with chemicals,

*B* is the number of eggs laid per gram of body weight of ticks of the group treated with chemicals.

The foregoing ratio was used to indicate the effectiveness of the chemicals tested.

By way of comparison, the same test was conducted with Control Chemicals I and II. Control Chemicals I and II are known as being powerful acaricidal preparations, their active ingredients being N'-(2-methyl-4-chlorophenyl)-N,N'-dimethyl formamidine and 1-naphthyl-N-methylcarbamate, respectively.

The results of the tests are shown in Table 1.

Table 1

| Compound No. | Inhibition Ratio of Oviposition by *Boophilus microplus* | Inhibition Ratio of Oviposition by *Haemaphysalis longicornis* |
|---|---|---|
| 2 | 100% | —% |
| 5 | — | 100 |
| 6 | 96.3 | 100 |
| 7 | 100 | 100 |
| 8 | 100 | 100 |
| 9 | — | 100 |
| 10 | 100 | 100 |
| 11 | 93.1 | 100 |
| 12 | 100 | 100 |
| 13 | 85.0 | 100 |
| 14 | — | 96.6 |
| 15 | — | 98.0 |
| 16 | 100 | — |
| 17 | 100 | 100 |
| 23 | 81.9 | — |
| 24 | — | 100 |
| 25 | 100 | 100 |
| Control Chemical I (110 γ/g) | 78.2 | — |
| Control Chemical II (110 γ/g) | 27.0 | — |
| Control (untreated) | 0 | 0 |

In the case of the compounds Nos. 6–12, 16–7 and 23–25, it was found that these compounds had fully satisfactory effectiveness in inhibiting oviposition even when the concentration was diluted to one-tenth of that indicated above.

TEST 2

Test of the combatting effect in killing of tick larvae of *Boophilus microplus* and *Haemaphysalis longicornis*

Groups of 50 to 100 larvae of *Boophilus microplus* and *Haemaphysalis longicornis* of about two weeks old placed in paper packets were immeresed for 2 to 5 minutes in an emulsified aqueous solution of the test compounds of a concentration of 100 ppm, and the larvae were incubated at 25° C. for 24 hours according to the procedure described by Stone and Haydock (1962), and the rate of the larvae killed were determined. The results of these tests are shown in Table 2. Each figure indicates mortality of unfed larvae after treatment with the test compounds.

Table 2

| Compound No. | Combatting Effect of Larvae of *Boophilus microplus* | Combatting Effect of Larvae of *Haemaphysalis longicornis* |
|---|---|---|
| 1 | —% | 98.0% |
| 3 | 96.4 | — |
| 4 | — | 80.3 |
| 5 | — | 100 |
| 6 | 74.6 | — |
| 8 | 68.5 | — |
| 9 | — | 100 |
| 12 | 86.5 | 82.2 |
| 13 | 92.8 | — |
| 14 | — | 80.3 |
| 16 | 100 | — |
| 17 | 100 | 100 |
| 18 | 100 | 100 |
| 19 | 81.8 | 86.6 |
| 20 | — | 96.4 |
| 21 | — | 100 |
| 22 | — | 82.5 |
| 23 | 100 | 99.1 |
| 24 | 99.5 | 99.1 |
| 25 | 91.2 | 100 |
| 26 | 81.9 | 86.4 |
| 27 | 77.8 | 91.1 |
| Control (untreated) | 0 | 0 |

TEST 3

Test of effectiveness in inhibiting the oviposition by *Boophilus microplus* as well as effectiveness in killing the adults thereof An emulsion was prepared in accordance with the foregoing Recipe 1, using as its active ingredient the compound No. 12. Several classes of spraying liquids having the concentrations indicated in Table 3 were prepared by diluting this emulsion with water. Ten female *Boophilus microplus* which had sucked blood fully were placed on a filter paper, and the liquid described above was sprayed onto the ticks with a glass sprayer in an amount such that the liquid would flow down the backs of the ticks. The ticks were then immediately transferred to a wet filter paper disposed in a Petri dish, and when the liquid on the backs of the ticks became somewhat dried, the dish was covered. The Petri dish was then held at a constant temperature of 30° C. for two weeks, after which the total amount of eggs laid was counted. During the time the Petri dish was held at a constant temperature, the inside of the Petri dish was maintained in a state of high humidity by dropping a small amount of water onto the filter paper daily. The effectiveness was judged by the rate of eggs laid by the several treated groups relative to the total eggs laid in the case of the ticks of the control group, which had been sprayed with only water. On the other hand, the effectiveness in killing the female adults was judged by observation of the presence or absence of deaths. The case where the presence of deaths was observed is indicated with the symbol (+), and the case where there were no deaths is indicated with the symbol (−).

The results obtained are shown in Table 3.

Table 3

| Concentration of Compound (%) | Rate of Eggs Laid (%) | Effectiveness in Killing Adults |
|---|---|---|
| 1 | 0 | (+) |
| 0.3 | 0 | (+) |
| 0.1 | 0 | (+) |
| 0.03 | 62.6 | (−) |
| 0.01 | 85.5 | (−) |
| 0.003 | 94.8 | (−) |

TEST 4

Test of the toxicity of the test compounds

Acute oral toxicity was determined by using male albino mice strain ddY, 5 weeks old. The test compounds were administered orally once and the $LD_{50}$ values were calculated after observing for a week. The results of these tests are shown in Table 4 with the $LD_{50}$ value of the control chemicals.

Table 4

| Compound No. | Acute Toxicity ($LD_{50}$) |
|---|---|
| 6 | 2,000 mg/kg (oral, mice) |
| 8 | 6,000 mg/kg (oral, mice) |
| 9 | 7,000 mg/kg (oral, mice) |
| 12 | >16,000 mg/kg (oral, mice) |
| 16 | 6,000 mg/kg (oral, mice) |
| 17 | 11,000 mg/kg (oral, mice) |
| Control Chemical I | 160 mg/kg (oral, mice) |
| Control Chemical II | 265 mg/kg (oral, mice) |
| | 630 mg/kg (oral, rats) |
| Control Chemical III | 70 mg/kg (oral, mice) |
| | 163 mg/kg (oral, rats) |
| Control Chemical IV | 56–230 mg/kg (oral, rats) |

Control Chemical III : O,O-diethyl O-(3,5,6-trichloro-2-pyridyl)phosphorothioate, "Chlorpyrifos"
Control Chemical IV : O,O-diethyl O-(3-chloro-4-methyl-7-coumarinyl)phosphorothioate, "Coumaphos"

What is claimed is:

1. A method of combatting ticks which comprises applying to the surface of the body of domestic animals infested with ticks a pesticidally effective amount of a carbodiimide of the formula

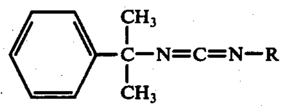

wherein R is a moiety selected from the group consisting of (1) aryclic alkyl containing 2–18 carbon atoms; (2) cyclohexyl;; (3) cyclohexyl substituted by 1–3 methyl groups (4) phenyl; (5) phenyl substituted by at least one moiety selected from the group consisting of alkyl having 1–4 carbon atoms, alkoxy having 1–4 carbon atoms and chlorine; (6) benzyl; (7) p-chlorobenzyl; and (8) phenylethyl.

2. The method of inhibiting the oviposition of ticks according to claim 1.

3. The method of killing eggs, larvae and adults of ticks according to claim 1.

4. The method of claim 1 wherein the carbodiimide is N-n-hexyl-N'-(2-phenyl-2-propyl)carbodiimide.

5. The method of claim 1 wherein the carbodiimide is N-cyclohexyl-N'-(2-phenyl-2-propyl)carbodiimide.

6. The method of claim 1 wherein the carbodiimide is N-n-heptyl-N'-(2-phenyl-2-propyl)carbodiimide.

7. The method of claim 1 wherein the carbodiimide is N-n-octyl-N'-(2-phenyl-2-propyl)carbodiimide.

8. The method of claim 1 wherein the carbodiimide is N-(2-ethyl-n-hexyl)-N'-(2-phenyl-2-propyl)carbodiimide.

9. The method of claim 1 wherein the cabodiimide is N-n-nonyl-N'-(2-phenyl-2-propyl)carbodiimide.

10. The method of claim 1 wherein the carbodiimide is N-(3,3,5-trimethylcyclohexyl)-N'-(2-phenyl-2propyl)carbodiimide.

11. The method of claim 1 wherein the carbodiimide is N-n-decyl-N'-(2-phenyl-2-propyl)carbodiidimde.

12. The method of claim 1 wherein the carbodiimide is N-n-dodecyl-N'-(2-phenyl-2propyl)carbodiimide.

13. The method of claim 1 wherein the carbodiimide is N-benzyl-N'-(2-phenyl-2-propyl)carbodiimide.

14. The method of claim 1 wherein the carbodiimide is N-α-phenylethyl-N'-(2-phenyl-2-propyl)carbodiimide.

15. The method of claim 1 wherein the carbodiimide is N-β-phenylethyl-N'-(2-phenyl-2-propyl)carbodiimide.

16. The method of claim 1 wherein the carbodiimide is N-p-chlorobenzyl-N'-(2-phenyl-2-propyl)carbodiimide.

17. The method of claim 1 wherein the carbodiimide is N-phenyl-N'-(2-phenyl-2-propyl)carbodiimide.

* * * * *